United States Patent [19]

Jaw

[11] Patent Number: 5,074,322
[45] Date of Patent: Dec. 24, 1991

[54] STRUCTURE OF STERILIZING HAND DRYER

[76] Inventor: Chin-Woei Jaw, No. 11, Alley 4, Lane 85, Chung Hua Rd., Hsin Tien City, Taiwan

[21] Appl. No.: 623,317

[22] Filed: Dec. 6, 1990

[51] Int. Cl.$^5$ .............................................. B08B 3/02
[52] U.S. Cl. ................... 134/56 R; 134/102; 134/200; 134/174; 134/201; 604/289
[58] Field of Search ................ 134/56 R, 102, 200, 134/174, 171, 181; 422/28, 292; 604/287

[56] References Cited

U.S. PATENT DOCUMENTS

| | | | |
|---|---|---|---|
| 2,677,381 | 5/1954 | Fisher | 134/56 R |
| 2,970,073 | 1/1961 | Prange | 604/289 X |
| 3,059,815 | 10/1962 | Parsons Jr. | 604/289 X |
| 3,416,544 | 12/1968 | Palva | 134/172 X |
| 3,683,896 | 8/1972 | Peplin | 604/289 X |
| 4,345,609 | 8/1982 | Nishizawa | 134/171 X |
| 4,670,010 | 6/1987 | Dragone | 604/289 X |
| 4,688,585 | 8/1987 | Vetter | 134/198 X |
| 4,742,836 | 5/1988 | Buehler | 134/201 X |
| 4,791,947 | 12/1988 | Holzberger | 134/172 X |
| 4,817,651 | 4/1989 | Crisp et al. | 134/181 X |

Primary Examiner—Frankie L. Stinson
Attorney, Agent, or Firm—Varndell Legal Group

[57] ABSTRACT

For sterilizing and air-drying the user's hands, a sterilizing hand dryer comprising an antiseptic solution spraying system for discharging antiseptic solution through a nozzle to sterilize the body limb inserted in a sterilizing chamber and detected by an electric eye, a hot air blower means for discharging hot air in said sterilizing chamber for drying said body limb, a control circuit for stopping the sterilizing hand dryer 3 seconds after removal of said body limb from said sterilizing air bath camber.

1 Claim, 3 Drawing Sheets

STRUCTURE OF STERILIZING HAND DRYER

BACKGROUND OF THE INVENTION

The present invention relates to sterilizing hand dryers, and more particularly relates to a sterilizing hand dryer which discharges antiseptic solution and hot air for sterilizing and drying the user's hands and which comprises a control circuit means to automatically cut off power supply 3 seconds after removal of the user's hands.

Effectively sterilizing the hand before or after working is very important in every hospital to eliminate the transmission of possible diseases or possible contamination. According to conventional methods, medical care people tend to wash the hands with soap or use absorbent cotton to apply antiseptic solution on the hands before or after working, or wear a pair of sterilized or disposable gloves for protection. Washing the hand with soap or antiseptic solution must be very careful or certain bacteria may be difficult to kill or remove from the hand. After washing, the hand must be immediately dries. During hand drying process, contamination may happen easily. If sterilized gloves are used, they must be sterilized again after each use. If disposable gloves are used, it will become a great expense to a hospital or a person.

SUMMARY OF THE INVENTION

The present invention has been accomplished under the circumstances in view. It is therefore the main object of the present invention to provide a sterilizing hand dryer which can effectively sterilize and dry the hand.

There is provided a sterilizing hand dryer in accordance with the present invention, comprising an electric eye installed at the top inside a rectangular housing for detecting the presence of the user's hands to trigger an IC control circuit to drive a pump to pump antiseptic solution for discharging through a nozzle for sterilizing the user's hands and to drive an electric heater and an electric fan to discharge hot air for drying the user's hands.

DETAILED DESCRIPTION OF THE PREFERRED EMBODIMENT

Figure 1:
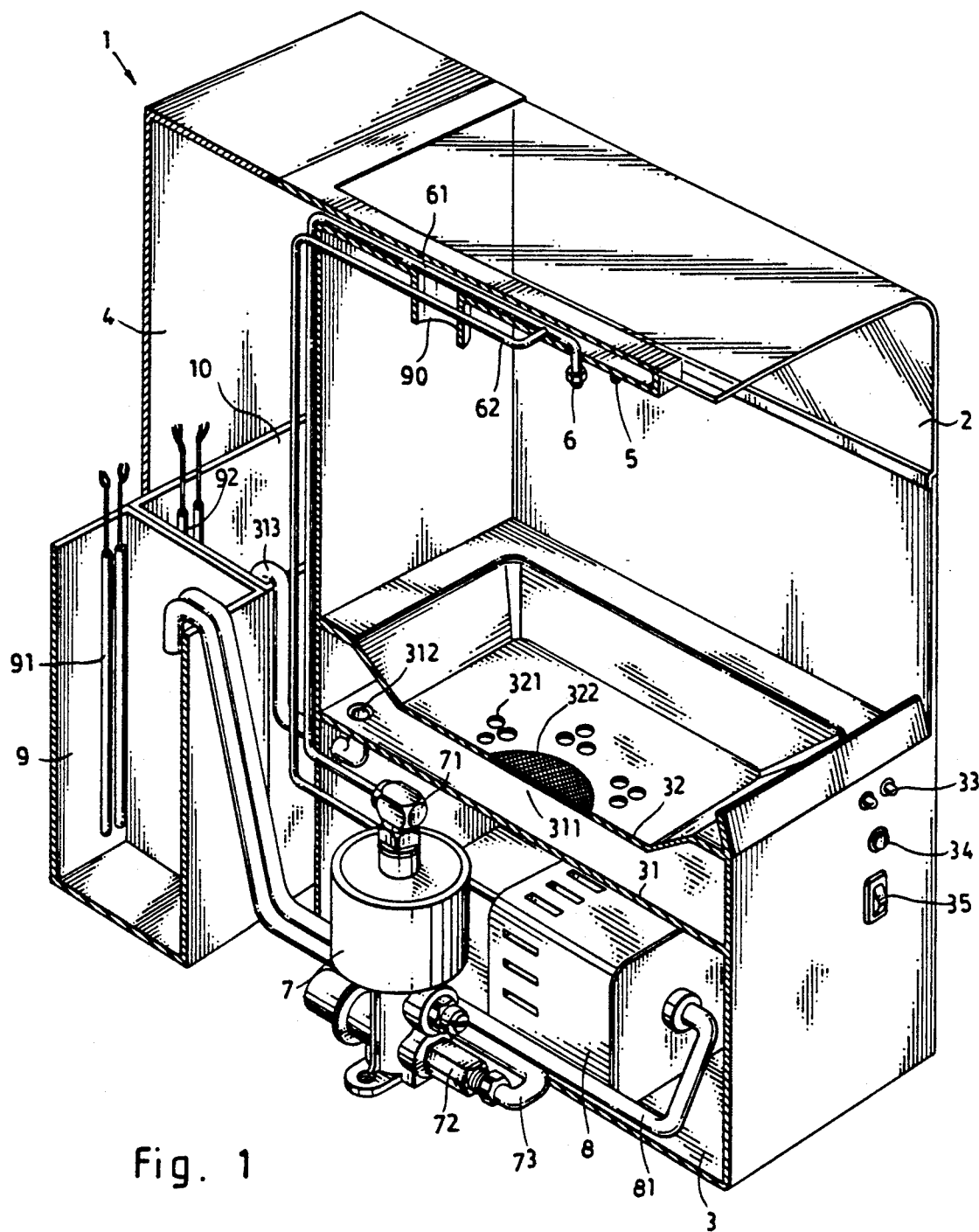
FIG. 1 is a perspective view of the preferred embodiment of the sterilizing hand dryer of the present invention.

Referring to FIG. 1, there is shown a sterilizing hand dryer embodying the present invention and generally comprised of a rectangular housing 1 defining therein a sterilizing chamber 2 at the top, an equipment compartment 3 at the bottom and a storage compartment 4 at one side. The storage compartment 4 defines therein an antiseptic solution supply chamber 9 separated from a waste solution receiving chamber 10 which is provided for collecting waste water discharged from the sterilizing chamber 2. There is mounted inside the housing 1 at the top of the sterilizing chamber 2 an electric eye 5, a stainless steel nozzle 6 and an air outlet 90. A supply tube 61 from feed head 71 of a high-pressure pump 7 which is installed inside the equipment compartment 3 is connected to the stainless steel nozzle 6. The supply tube 61 has a branch tube 62 connected to an electromagnetic valve 8 which is installed inside the equipment compartment 3. The air outlet 90 is connected to an electric heater (not shown), which is also installed inside the equipment compartment 3, for discharging of hot air for drying an user's arms and hands which are inserted in the sterilizing chamber 2. At the top of the equipment compartment 3, there is made a sink 32 which comprises a circular reflector 322 disposed right below the electric eye 5, and a plurality of draining holes 321 around said circular reflector 322. There is a division plate 31 fastened inside the equipment chamber 3 below the sink 32 and defining with the sink 32 a water reservoir chamber 311, which has a drain trap 312 at one corner. On the outer side of the equipment compartment 3 there is provided two alarm lamps 33, a timer 34 and a power switch 35. Further, the high pressure pump 7 has an intake port 72 (opposite to the feed head 71) connected to the antiseptic solution supply chamber 9 through a supply tube 73, and the electromagnetic valve 8 has outlet port connected to the supply chamber 9 through a return pipe 81. The drain trap 312 of the division plate 31 is connected to the waste solution receiving chamber 10 through a drain tube 313. There is also provided an IC control circuit (not shown) at the inner top of the storage compartment 4 for controlling two inductors 91 and 92 which are respectively fastened in the antiseptic solution supply chamber 9 and the waste solution receiving chamber 10 and connected to the alarm lamps 33.

Figure 2:
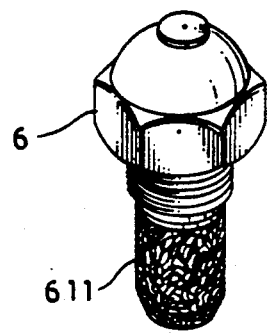
FIG. 2 is a perspective view of the stainless steel nozzle of the preferred embodiment of the sterilizing hand dryer of the present invention.
Figure 3:
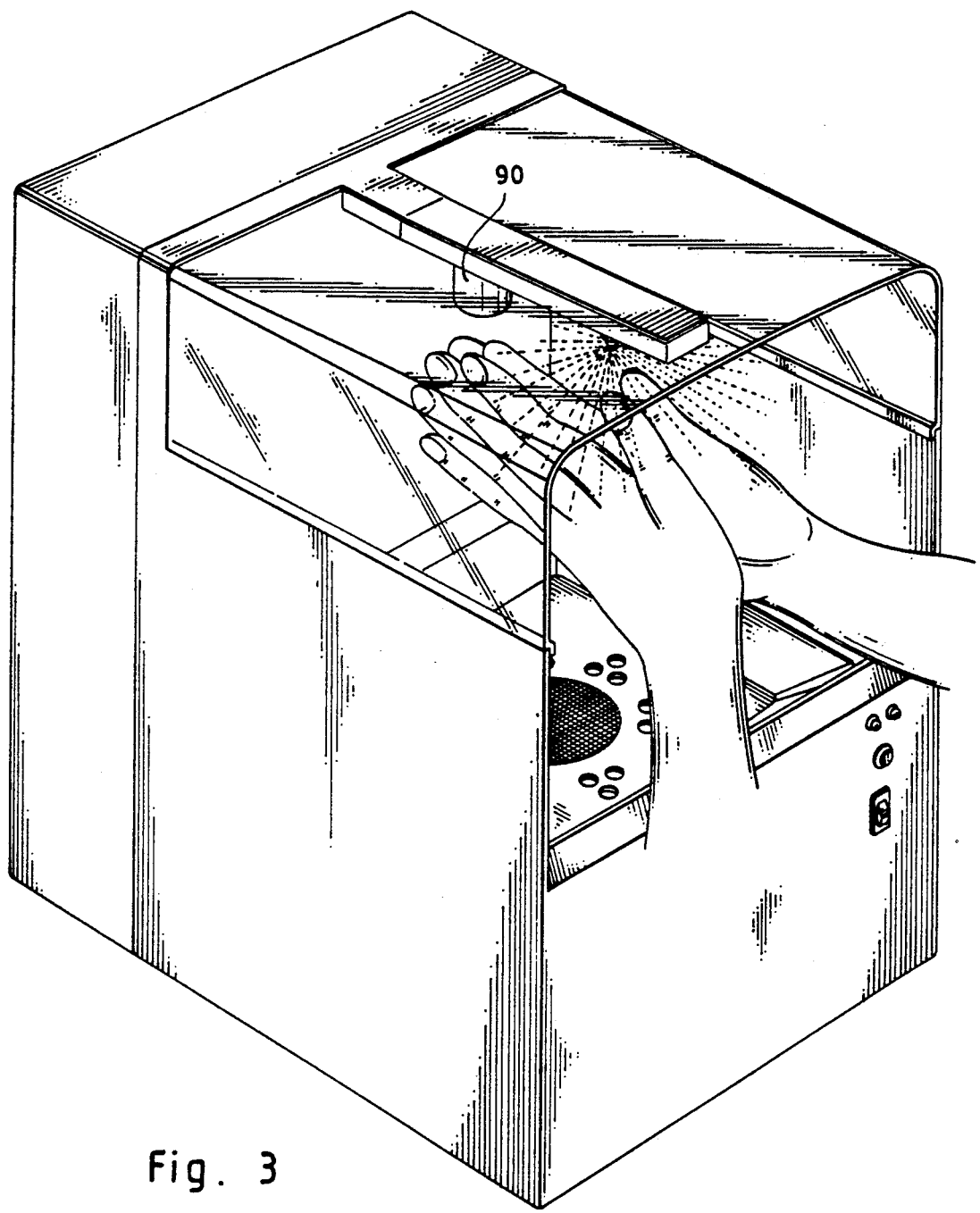
FIG. 3 is a schematic drawing illustrating the operation of the present invention in sterilizing and drying an user's hands.

The operation of the present invention is outlined hereinafter with reference to FIG. 3. After the power switch 35 is switched on and the timer 34 is set, the hand of the user which are inserted in the sterilizing chamber 2 are immediately sensed by the electric eye 5 to trigger the IC control circuit to control the operation of the electromagnetic valve 8, permitting antiseptic solution to be pumped from the antiseptic solution supply chamber 9 into the supply tube 72 by the high pressure pump 7 for delivery through the feed head 71 and the supply tube 61 and for further discharging through the stainless steel nozzle 6. As soon as the setting time is up, the electromagnetic valve 8 is automatically opened, permitting discharged antiseptic solution to flow through the branch tube 62, the electromagnetic valve 8 and the return pipe 81 to the antiseptic solution supply chamber 9. Please see FIG. 2, when the electromagnetic valve 8 is closed, the high pressure pump 7 gives antiseptic solution a pressure of 7 kg/sec toward the stainless steel nozzle 6, causing antiseptic solution to discharge through the stainless steel nozzle 6 via a filter element 611 which is attached to the stainless steel nozzle 6 at the rear end; when the electromagnetic valve 8 is opened, the pressure in the supply tube 61 is reduced, permitting antiseptic solution to flow back to the high pressure pump 7 through the branch tube 62. Immediately after the electromagnetic valve 8 is opened to stop discharging of antiseptic solution, an electric heater and an electric fan (not shown) are turned on to produce 45 hot air through the air outlet 90 for drying user's hands. As soon as user's hands are removed out of the sterilizing chamber 2 after having been dried, the electric eye 5 gives a signal to the IC control circuit to cut off power supply three seconds after triggering. Waste antiseptic solution collected in the sink 32 immediately flows through the drain holes 321 into the water reservoir chamber 311 from which the collected waste antiseptic solution is further discharged through the drain trap 312 and the drain tube 313 to the waste solution receiving chamber 10. When waste solution in the waste solution receiving chamber 10 is over the predetermined limit or antiseptic solution in the antiseptic solution supply chamber 9 is below the predetermined limit, the inductor 92 or 91 immediately triggers the corresponding alarm lamp 33 to give a visual signal for warning.

I claim:

1. For sterilizing and air-drying the user's arms and hands, an apparatus comprising:
  a rectangular housing defining therein a sterilizing chamber at the top, an equipment compartment at the bottom and a storage compartment at one side, said sterilizing chamber having at least an opening for receiving a body limb, said equipment compartment having a sink at the top and a water reservoir chamber beneath said sink, said storage compartment defining therein an antiseptic solution supply chamber separated from and a waste solution receiving chamber, said antiseptic solution supply chamber being provided for containing clean antiseptic solution, said waste solution receiving chamber being provided for collecting waste water from said sink through said water reservoir chamber;
  an antiseptic solution spraying system comprising a high pressure pump for pumping antiseptic solution from said antiseptic solution supply chamber to a nozzle means for spraying in said sterilizing chamber;
  an antiseptic solution recirculation system comprising an electromagnetic valve means for recirculation of antiseptic solution from said antiseptic solution spraying system to said antiseptic solution supply chamber;
  a detector means for detecting the presence of body limb in said sterilizing chamber;
  a hot air blower means comprising an electric heater and an electric fan installed inside said equipment compartment for discharging hot air in said sterilizing air chamber through a discharge tube;
  a first alarm system comprising an inductor disposed inside said waste solution receiving chamber to trigger a first alarm lamp to give visual alarm signal when waste solution collected in said waste solution receiving chamber over a predetermined limit;
  a second alarm system comprising an inductor disposed inside said antiseptic solution supply chamber to trigger a second alarm lamp to give visual alarm signal when antiseptic solution contained in said antiseptic solution supply chamber below a predetermined level;
  a control circuit means triggered by said detector means to control said antiseptic solution spraying system, said antiseptic solution recirculation system, said detector means, said hot air blower means, said first alarm system and said second alarm system to operate upon detection of body limb in said sterilizing chamber by said detector means.

* * * * *